(12) United States Patent
Pfeiffer et al.

(10) Patent No.: US 8,531,665 B1
(45) Date of Patent: Sep. 10, 2013

(54) SMALL VOLUME CELL

(75) Inventors: Galen L. Pfeiffer, Lincoln, NE (US);
Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 411 days.

(21) Appl. No.: 12/807,461

(22) Filed: Sep. 7, 2010

Related U.S. Application Data

(62) Division of application No. 12/220,415, filed on Jul. 24, 2008, now Pat. No. 7,817,266.

(60) Provisional application No. 60/961,996, filed on Jul. 26, 2007.

(51) Int. Cl.
*G01J 4/00* (2006.01)
*G01N 1/10* (2006.01)

(52) U.S. Cl.
USPC .......................................... 356/369; 356/246

(58) Field of Classification Search
None
See application file for complete search history.

(56) References Cited

U.S. PATENT DOCUMENTS

| | | | |
|---|---|---|---|
| 4,017,190 A | 4/1977 | Fischel | 356/40 |
| 4,565,446 A | 1/1986 | Chu | 356/246 |
| 4,818,103 A | 4/1989 | Thomas et al. | 356/72 |
| 5,313,264 A * | 5/1994 | Ivarsson et al. | 356/445 |
| 6,046,805 A * | 4/2000 | Kawamura et al. | 356/368 |
| 6,937,341 B1 | 8/2005 | Woollam et al. | 356/4.36 |
| 7,223,609 B2 * | 5/2007 | Anvar et al. | 436/165 |
| 7,260,980 B2 * | 8/2007 | Adams et al. | 73/31.05 |
| 7,389,679 B2 | 6/2008 | Battiston et al. | 73/61.79 |
| 7,426,030 B1 * | 9/2008 | Liphardt et al. | 356/369 |
| 7,535,570 B2 * | 5/2009 | Muraishi | 356/445 |
| 8,130,375 B1 * | 3/2012 | Pfeiffer et al. | 356/246 |
| 2009/0027679 A1 * | 1/2009 | Pfeiffer et al. | 356/440 |
| 2009/0061331 A1 * | 3/2009 | Nakano | 250/363.01 |

* cited by examiner

*Primary Examiner* — Gregory J Toatley
*Assistant Examiner* — Juan D Valentin, II
(74) *Attorney, Agent, or Firm* — James D. Welch

(57) ABSTRACT

An ellipsometer system comprising a small internal volume cell having fluid entry, and exit ports wherein bubble traps are present in a bifurcated fluid pathway continuous with the fluid exit port. There further being present input and output apertures, for entering and exiting electromagnetic radiation, positioned to allow causing a beam of electromagnetic radiation to impinge on a sample substrate at a location thereon at which, during use, fluid contacts; as well as methodology of its use.

6 Claims, 2 Drawing Sheets

SMALL VOLUME CELL

CROSS-REFERENCE TO OTHER APPLICATIONS

This application is a Divisional of Parent application Ser. No. 12/220,415 Filed Jul. 24, 2008, and therevia Claims Benefit of Provisional 60/961,996 Filed Jul. 26, 2007.

TECHNICAL FIELD

The present invention relates to cells for containing fluid to be investigated by electromagnetic radiation, and more particularly to a small internal volume cell comprising fluid entry and exit ports including bubble traps, and input and output apertures for entering and exiting electromagnetic radiation, as well as methodology of use.

BACKGROUND

It is known to apply cells for receiving fluids and investigating sample in said fluid with electromagnetic radiation. For instance, a patent to Woollam et al., U.S. Pat. No. 6,937,341 that enables simultaneous investigation of a sample in a fluid with two beams of electromagnetic radiation.

A computer search was conducted to identify patents which discuss small fluid cells and ellipsometry, and none were found. However, a patent to Battiston et al., U.S. Pat. No. 7,389,679 was identified as it does disclose cell for containing small amounts of fluid. The design of the cell, however, is very different from that of the present invention. In particular fluid entry ports are at a lower extent of the 679 system which means bubbles rise through entered fluid. As disclosed herein, in the Detailed Description Section and Drawings, the present invention system provides for a very different fluid entry configuration.

Need remains for additional small cells for use in investigating fluid samples with electromagnetic radiation, and in particular small cells which provide means for reducing the effect of bubbles caused by entry of the fluid into said small cell.

DISCLOSURE OF THE INVENTION

The present invention is a small internal volume cell comprising a sample substrate at a lower extent thereof, and laterally separated fluid entry and exit ports at an upper extent thereof, as viewed in elevation. The small internal volume cell further comprises input and output apertures for entering and exiting, respectively, a beam of electromagnetic radiation, which are affixed to laterally separated sides of the small volume cell, to allow entry and exit, respectively, of a beam of electromagnetic radiation known angles-of-incidence and reflection, as viewed in frontal elevation. Said small internal volume cell is characterized by the presence of at least one bubble accumulating trap region in a fluid exit pathway to said exit port, which bubble trap(s) serve to accumulate bubbles produced during the entry and exit of fluid, into and from, said small internal volume cell.

In use, fluid is caused to enter said fluid input port and is directed to be contact said sample substrate, then said fluid exits via said exit port. During use, simultaneously, a beam of electromagnetic radiation is caused to enter said input aperture, reflect from said sample substrate near the location at which said fluid is caused to contact said sample substrate, and exits said output aperture.

The input port is continuous with a single fluid entry pathway that ends at a point above the sample substrate, near a location thereon at which fluid entered to said input port, contacts during use. And, said output port is continuous with a fluid exit pathway which bifurcates into two laterally opposed pathways that serve to receive fluid which is presented to said sample substrate, and flows therefrom in laterally opposed directions.

The preferred embodiment of the cell has an internal volume which is on the order of one-half (0.5) milliliter or less, and can further comprise temperature control means for controlling the temperature of said sample substrate.

The small internal volume cell can be further characterized by a reduced diameter aperture region between the input aperture and the sample substrate, and the sample substrate can be selected to be of a composition so as to selectively secure thereto a component in a fluid presented thereto, to the exclusion of other components. An example is to provide a sample substrate which is composed of gold on glass, and provide a fluid which includes biotin. The effective sample which the electromagnetic beam impinges on becomes biotin attached to the gold. Another example is that a substrate to which is applied "dirt" can be affected by a fluid which contains "soap". The electromagnetic beam can monitor the removal of the dirt as the soap flows thereby. Still another, very basic, example is to provide an effectively inert sample substrate and flow a fluid for which the optical constants are to be determined. In such examples, it is noted that the fluid is typically, but not necessarily, a liquid. That is, it can be, for instance, a gas. The present invention then includes providing a sample substrate which has a composition appropriate to the task, said composition being, for instance, characterized as a selected from the group:
  chemically inert;
  chemically reactive with at least one component in a fluid.
  chemically reactive with one component in a fluid and not other components.

A method of investigating a sample present in a fluid comprises the steps of:
  a) providing a cell as just described above;
  b) causing sample containing fluid to be entered into said cell internal volume, with any bubbles produced accumulating in said bubble traps;
  c) causing a beam of electromagnetic radiation to enter said input aperture, proceed through said fluid, reflect from said sample substrate and exit said output aperture;
  d) causing said exiting beam of electromagnetic radiation to enter a data detector.

Said method can further comprise:
  e) performing at least one selection from the group consisting of:
    storing at least some data provided by said data detector in machine readable media;
    analyzing at least some of the data provided by said data detector and storing at least some of the results of said analysis in machine readable media;
    displaying at least some data provided by said data detector by electronic and/or non-electronic means;
    analyzing at least some of the data provided by said data detector and displaying at least some of the results of said analysis by electronic and/or non-electronic means;
    causing at least some data provided by said data detector to produce a signal which is applied to provide a concrete and tangible result;

analyzing at least some of the data provided by said data detector and causing at least some thereof to produce a signal which is applied to provide a concrete and tangible result.

Said method can further comprises providing a polarized electromagnetic beam in step c.

The present invention is also an ellipsometer system that comprises:
- a source of a beam of electromagnetism;
- a polarizer;
- a small internal volume cell comprising a sample substrate at a lower extent thereof, said small internal volume cell further comprising laterally separated fluid entry and exit ports at an upper extent thereof and input and output apertures for entering and exiting a beam of electromagnetic radiation affixed to laterally separated sides thereof, to allow entry and exit at known angles-of-incidence and reflection, as viewed in frontal elevation;
- said small internal volume cell being characterized by the presence of at least one bubble accumulating trap region in a fluid exit pathway to said exit port for accumulating bubbles produced during the entry and exit of fluid from said small volume cell;
- said small internal volume cell being further characterized in that said input port is continuous with a single fluid entry pathway that ends at a point above the sample substrate, at a location thereon near which fluid entered to said input port, contacts during use; and said output port is continuous with a fluid exit pathway which bifurcates into two laterally opposed pathways that serve to receive fluid which contacts said sample substrate, and flows therefrom in laterally opposed directions;
- such that in use, while fluid is caused to enter said input port and contact said sample substrate, then exit via said exit port, a beam of electromagnetic radiation is caused to enter said input aperture, reflect from said sample substrate near the location at which said fluid contacts said sample substrate, and exit said output aperture;
- a polarizer; and
- a detector.

Again, the small internal volume of small internal volume cell can be about one-half (0.5) milliliter or less; there can be present a temperature control means for controlling the temperature of said substrate for supporting a sample of said internal volume of small internal volume cell; the internal volume of small internal volume cell can be further characterized by a reduced diameter aperture region between the input aperture and the sample substrate thereof; there can be at least one compensator between said polarizer and analyzer; and said source of a beam of electromagnetism can be monochromatic or spectroscopic.

The invention will be better understood by reference to the Detailed Description Section of this Specification, in combination with the Drawings.

DETAILED DESCRIPTION

Figure 1:
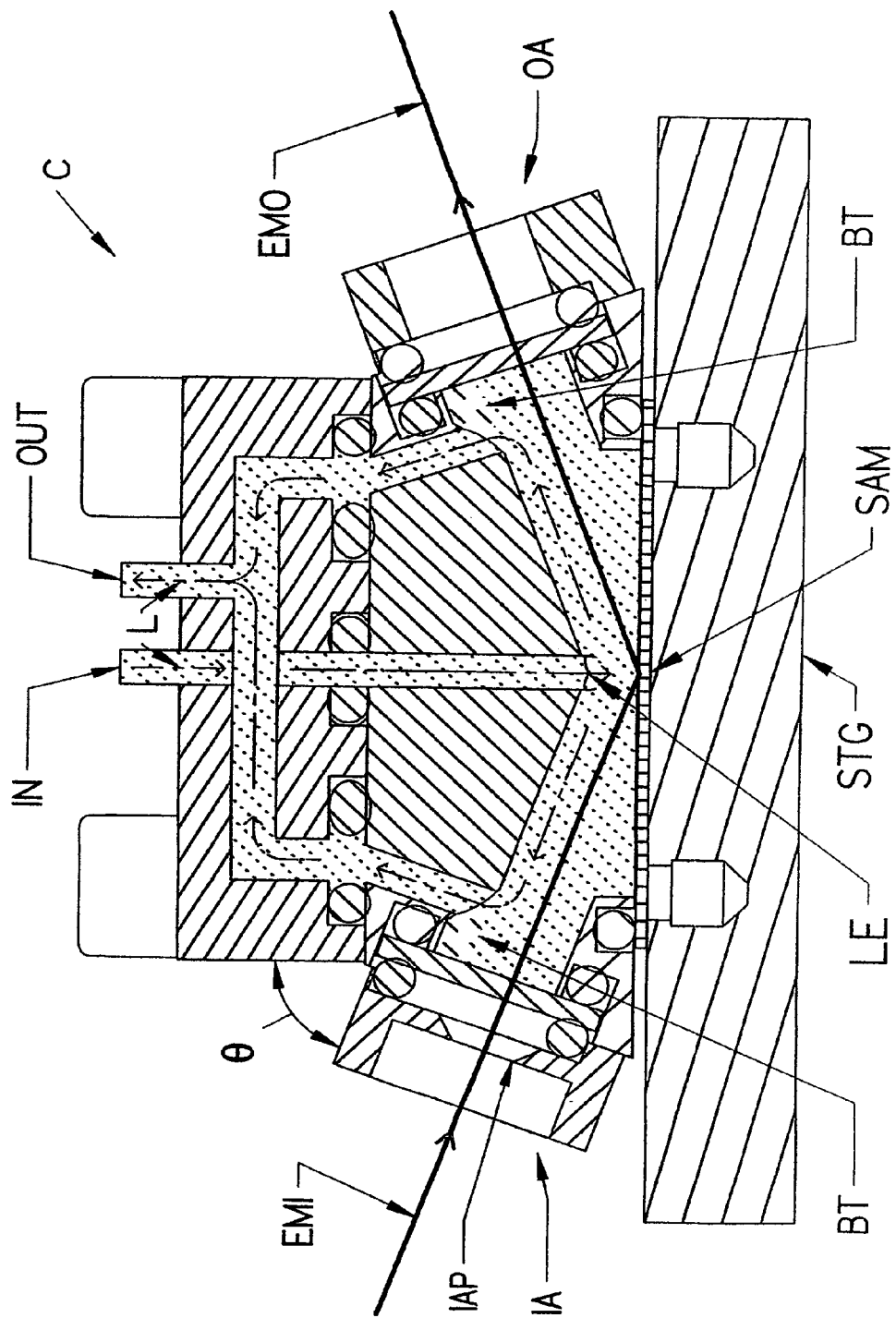
FIG. 1 shows a representation of the present small internal volume cell (C), in frontal elevation.

Turning now to the Drawings, there in shown in FIG. 1 a representation of the Present Invention Small Internal Volume Cell (C). Shown are an effective Sample Substrate (STG) at a lower extent thereof. Said Small Internal Volume Cell (C) further comprises Fluid (L) Entry (IN) and Exit (OUT) Ports and Bubble Traps (BT) in pathways to said Exit (OUT) Port, and Input (IA) and Output (OA) Apertures for entering (EMI) and exiting (EMO) a Beam of Electromagnetic Radiation. Said Entry (IN) and Exit (OUT) Ports are shown to be laterally separated from one another atop said Small Internal Volume Cell (C), and said Input (IA) and Output (OA) Apertures for entering (EMI) and exiting (EMO) a Beam of Electromagnetic Radiation are affixed to laterally separated sides of said Small Internal Volume Cell (C) to allow entry at a known oblique angle-of-incidence, (eg. $\theta=70$ degrees), as viewed in the FIG. 1 frontal elevation. Said Small Internal Volume Cell (C) is distinguished by the presence of said Bubble Accumulating Trap (BT) regions in at least one pathway to said Exit (OUT) port, for accumulating bubbles produced during the entry and exit of fluid from said Small Internal Volume Cell (C). Note that FIG. 1 shows that the preferred embodiment provides two pathways for fluid to follow to the Exit (OUT) Port. FIG. 1 shows that in use, fluid (L) which is entered to Input (IN) Port exits onto said Sample Substrate (STG) via a Fluid Exit (LE) opening at the end of a Fluid (L) input pathway, at a location thereupon from which a Beam of Electromagnetic Radiation (EMI) is caused to reflect.

It is further noted that associated with the Input Aperture (IA) is a Reduced Diameter Aperture Region (IAP). This serves to diminish interaction of the entered Beam of Electromagnetic Radiation (EMI) with sides of the pathway through which it proceeds to the Sample Substrate (STG). That is, reflections from the sides of the effective bore between the Bubble Traps (BT) and the Sample Substrate (STG) are greatly reduced over what they would be if the Reduced Diameter Aperture Region (IAP) were not present.

It is to be understood that the Sample Substrate (STG) can be of various compositions to interact with components deposited thereonto from the Fluid (L). For instance, the Sample Substrate (STG) can be, but does have to be, comprised of a material to which some component in a Fluid (L) attaches, to the exclusion of other components. That is, the composition of the Sample Substrate (STG) can be selected so that it secure thereto a component in a fluid, to the exclusion of other components. While the Sample Substrate (STG) can alone comprise a Sample (SM), when a Component from a fluid is affixed thereto, the combination of the fluid component in combination with the Sample Substrate (STG), form a Sample (SAM).

Note the presence of "O" rings, (shown generally as circles), which, in the case of the Input (IA) and Output (OA) Apertures for entering (EMI) and exiting (EMO) a Beam of Electromagnetic Radiation, serve to reduce stress induced effects that can affect Electromagnetic beam characteristics.

It is disclosed that the Small Internal Volume Cell (C) can be modified to provide a single Port, such as Input Port (IA), which serves to both enter (EMI) and exit (EMO) a Beam of Electromagnetic Radiation. The modification involves placing a mirror where the Output Aperture (OA) is shown in FIG. 1.

Figure 2:
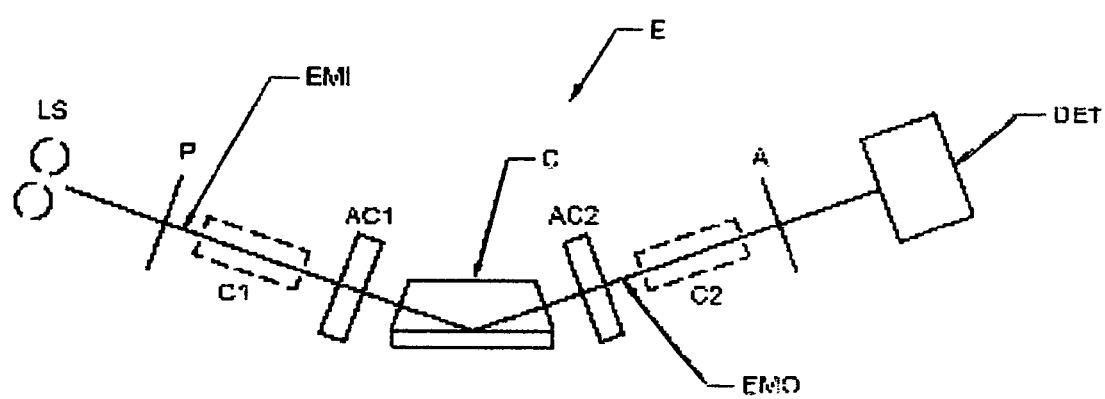
FIG. 2 shows a general elemental configuration of an ellipsometer system (E) which can be applied in combination with the small internal volume cell (C).

FIG. 2 is included to show a general elemental configuration of an Ellipsometer System (E) which can be applied in combination with the small internal volume cell (C). Note there is present a Source (LS) of a Beam of electromagnetic radiation which is directed to pass through a Polarizer (P) and appear as (EMI) which enters the Small Internal Volume Cell (C), interacts with a fluid sample therein, exits and passes through an Analyzer (A) and enters a Detector (DET). Note also identified are optional Compensators (C1) (C2), which can be stationary or rotated in use, and general representation of "additional elements" (AC1) (AC2) which might include, for instance, focusing elements. In use the Polarizer (P) imposes a state of polarization on Beam (EMI), which is changed by interaction with the fluid sample in the Small Internal Volume Cell (C), then monitored by the Analyzer and the Detector (DET).

It is noted that the terminology "Sample" as used herein can refer to a fluid per se. which contacts the Sample Substrate (STG), or components in said fluid which deposit on, or attach to, the Sample Substrate (STG).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer system comprising:
   a source of a beam of electromagnetism;
   a polarizer;
   a small internal volume cell comprising a sample substrate at a lower extent thereof, said small internal volume cell further comprising laterally separated fluid entry and exit ports at an upper extent thereof and input and output apertures for entering and exiting a beam of electromagnetic radiation affixed to laterally separated sides thereof, to allow entry and exit at known angles-of-incidence and reflection, as viewed in frontal elevation;
   said small internal volume cell being characterized by the presence of at least one bubble accumulating trap region in a fluid exit pathway to said exit port for accumulating bubbles produced during the entry and exit of fluid from said small volume cell;
   said small internal volume cell being further characterized in that said input port is continuous with a single fluid entry pathway that ends at a point above the sample substrate, at a location thereon near which fluid entered to said input port, contacts during use; and said output port is continuous with a fluid exit pathway which bifurcates into two laterally opposed pathways that serve to receive fluid which contacts said sample substrate, and flows therefrom in laterally opposed directions;
   such that in use, while fluid is caused to enter said input port and contact said sample substrate, then exit via said exit port, a beam of electromagnetic radiation is caused to enter said input aperture, reflect from said sample substrate at or near the location at which said fluid is caused to contact said sample substrate, and exit said output aperture;
   an analyzer; and
   a detector.

2. An ellipsometer system as in claim 1 wherein the small internal volume of small internal volume cell is about one-half (0.5) milliliter or less.

3. An ellipsometer system as in claim 1 which further comprises a temperature control means for controlling the temperature of said sample substrate of said internal volume of small internal volume cell.

4. An ellipsometer system as in claim 1, wherein the internal volume of small internal volume cell is further characterized by a reduced diameter aperture region between the input aperture and the sample substrate thereof.

5. An ellipsometer system as in claim 1 which further comprises at least one compensator between said polarizer and analyzer.

6. An ellipsometer system as in claim 1 in which said source of a beam of electromagnetism is selected from the group consisting of:
   mono-chromatic; and
   spectroscopic.

* * * * *